United States Patent [19]

Grifols Lucas

[11] Patent Number: 4,671,320
[45] Date of Patent: Jun. 9, 1987

[54] ADJUSTABLE VALVE FOR LIQUIDS FOR EQUIPMENT HAVING A MEDICAL APPLICATION

[76] Inventor: Victor Grifols Lucas, Numancia 187, Barcelona, Spain

[21] Appl. No.: 886,186

[22] Filed: Jul. 16, 1986

[30] Foreign Application Priority Data

Jul. 19, 1985 [ES] Spain .................................... 545.674
Aug. 1, 1985 [ES] Spain .................................... 288.855

[51] Int. Cl.⁴ ........................ F16K 37/00; F16L 55/14
[52] U.S. Cl. ...................................... 137/556.3; 251/4
[58] Field of Search .................. 251/4, 6–8; 137/556.3; 604/250

[56] References Cited

U.S. PATENT DOCUMENTS

| 2,234,052 | 3/1941 | Luenz | 137/556.3 |
| 2,313,550 | 3/1943 | Huber | 251/7 |
| 2,314,767 | 3/1943 | Burrell | 251/8 |
| 2,416,391 | 2/1947 | Hixson | 251/4 |
| 2,422,921 | 6/1947 | Nier et al. | 251/4 |
| 2,902,248 | 9/1959 | Barton et al. | 251/8 |
| 4,493,710 | 1/1985 | King et al. | 604/250 |
| 4,575,041 | 3/1986 | Hu | 251/4 |

Primary Examiner—Martin P. Schwadron
Assistant Examiner—Sheri M. Novack
Attorney, Agent, or Firm—Darby & Darby

[57] ABSTRACT

Disclosed is an adjustable valve for liquid including a flexible tubular body having a first and a second end. The tubular body is capable of elongation along the longitudinal axis. Provided within the flexible tubular body is a substantially cylindrical rigid body the rigid having a diameter smaller than the inside diameter of the flexible tubular body to form a radial clearance between the rigid body and the inside surface of the flexible tubular body. Means for elongating the flexible tubular body along the longitudinal axis about the rigid body are also included, whereby elongation of the flexible tubular body reduces the radial clearance.

10 Claims, 16 Drawing Figures

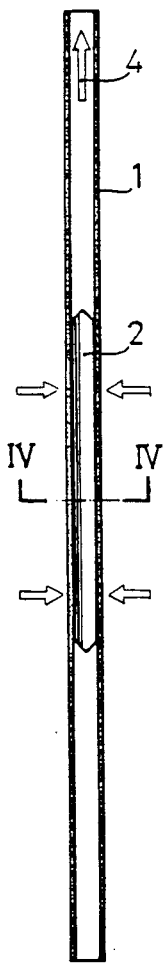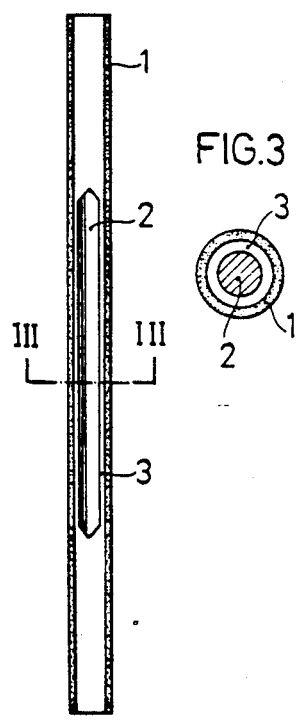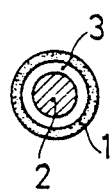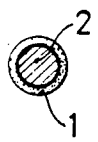

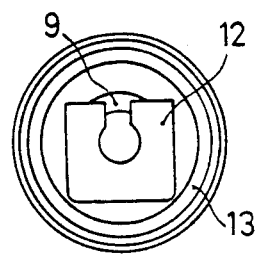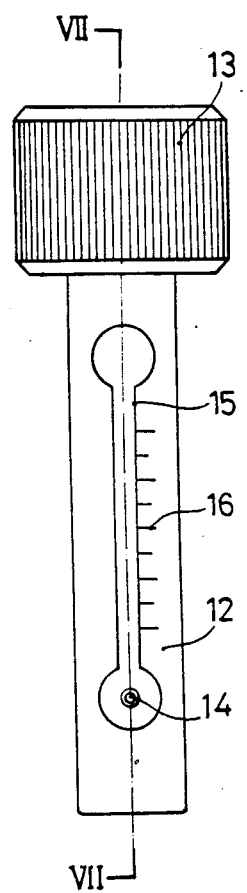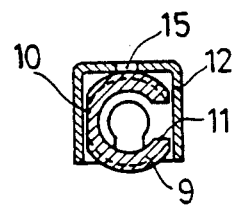

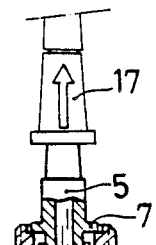
FIG. 14
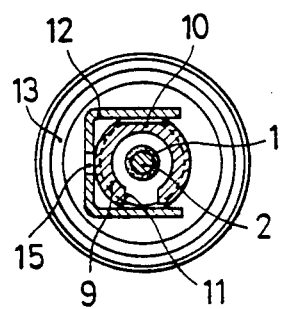
FIG. 16
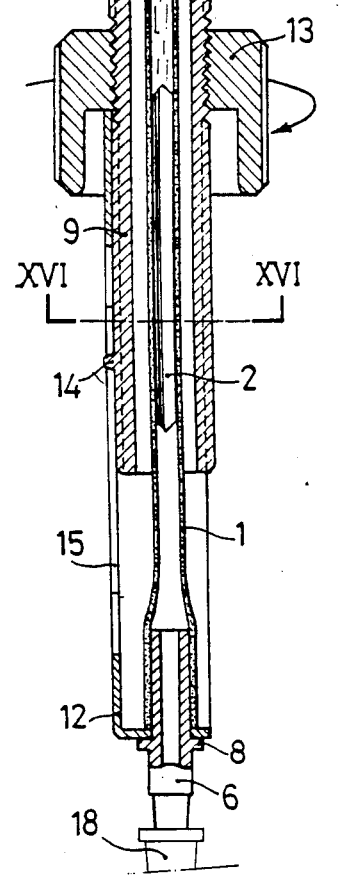

ADJUSTABLE VALVE FOR LIQUIDS FOR EQUIPMENT HAVING A MEDICAL APPLICATION

This Patent of Invention relates to a valve of original design applicable to apparatus of a medical type and particularly to intravenous infusion and transfusion equipment, as also for parenteral feeding.

As is known, in medical applications of the type referred to, i.e. intravenous infusions and transfusions, valves are required to control the flowrate of the liquid being administered, which valves require to have a number of specific features. In the first place, they must be capable of a fine adjustment, adjusting the flowrate supplied between limits with very low fluctuations, namely, the flow rate must be stable. Furthermore, they must be very cheap to manufacture to allow the generalised use of such valves in intravenous infusion and transfusion equipment, whereby they may be more frequently changed, since it is less costly for the application of new products in the medical treatment or even for their frequent disposal.

Furthermore, this type of valve must allow for being sterilised, both singly and when integrated in the corresponding equipment.

These features are achieved by the valve of the present Patent of Invention, said valve having original functional and constructional features.

Essentially, the valve of the present Patent of Invention is based on the principle of adjusting the amount of liquid flowing along a tube by varying the size of the cylindrical annulus between the inner walls of the tube and a cylindrical core, which may be solid or not, having constant dimensions and being positioned in the interior of the said tube, adjusting the effective inside diameter of the tube containing the inner core, such that the liquid flow may be precisely varied. To obtain such variation, the present invention relies on the outer tube, within which the cylindrical core is positioned, being a tube of rubber, silicone, plastics or other material having resilient properties, namely, that it may recover its original dimensions after having been subjected to tensile, compression or other stresses, so that when an axial pull is applied thereto, the diameter of the tube is reduced both externally and internally, with the clearance between the inner walls of the tube and the outer walls or surface of the constant diameter internal cylindrical core reducing progressively. In this way the effective passage of the liquid flowing inside the flexible tube is varied.

To attain its object, the present invention is based on the flexible outer tube having recovery properties allowing the outer tubular member to recover its original diameter when the axial pull or compression thereon is relieved.

To produce the longitudinal pull on the tubular member, the valve of the present Patent of Invention may adopt many solutions, which are based simply on applying a longitudinal pull of variable magnitude to the tubular member.

In a preferred embodiment, the flexible tubular member is fixed between two end mouth pieces, each of which is attached to a portion of the external conductive tube for the liquid to be supplied, there being provided a longitudinal stretching device for the flexible tube, comprising a generally square sectioned outer casing in the inside of which there is housed an externally threaded tubular member which may receive an axially fixed nut which, on rotating, causes the axial movement of said hollow threaded cylindrical body, which movement is transmitted to the flexible tube on abutting a flange of one of the end mouth pieces attached to said flexible tube.

For a better understanding, there are attached as an example, explanatory drawings of the valve of the present Patent of Invention.

FIGS. 1 and 2 are respective views in longitudinal section of the flexible tubular member with the internal stoppering body, respectively, in a rest position corresponding to the open position of the valve and to a closed position thereof.

FIGS. 3 and 4 are respective views in cross section along the lines III—III and IV—IV of FIGS. 1 and 2.

FIG. 8 is an end plan view of FIG. 6, and FIG. 9 is a cross section view on the line IX—IX of FIG. 6.

FIG. 10 is an outside elevation view of the unit of FIG. 6.

FIGS. 14 and 15 are respectively a longitudinal section and an external view of the valve of the present Patent of Invention in a stretched position of the flexible tubular member, namely in a closed position.

FIG. 16 is a cross section view on the line XVI—XVI of FIG. 14.

Figure 5:
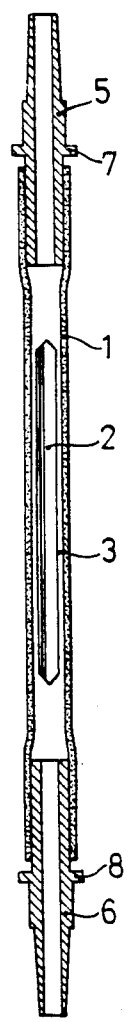
FIG. 5 is a longitudinal section view showing the preferred assembly of the tubular member in fixing end pieces.
Figure 6:
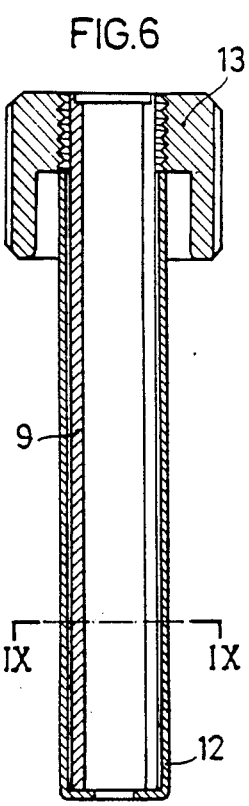
FIGS. 6 and 7 are respective views in longitudinal section, on mutually perpendicular planes, of the unit formed by the outer square sectioned body, the internal externally threaded tubular member and the adjusting nut.
Figure 7:
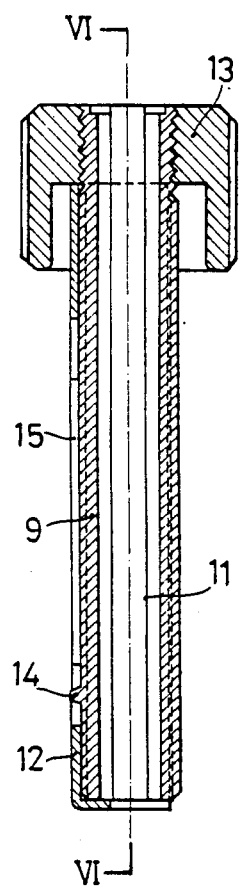
Figure 13:
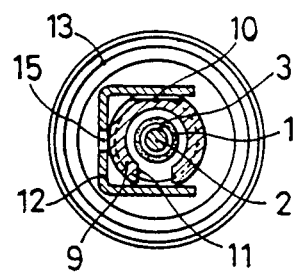
FIG. 13 is a cross section view on the line XIII—XIII of FIG. 11.
Figure 11:
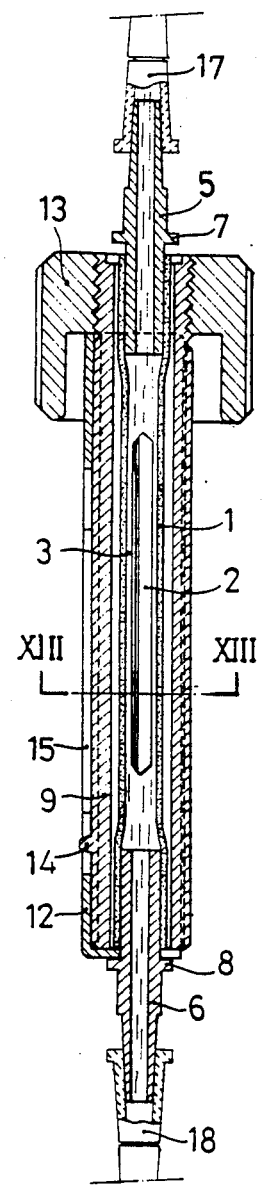
FIGS. 11 and 12 are respectively a longitudinal section view and an external view of the valve unit of the present invention, in the open position.
Figure 12:
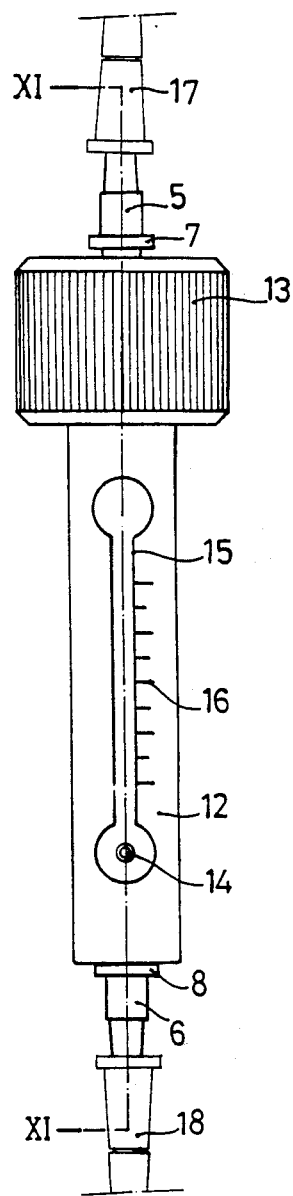
Figure 15:
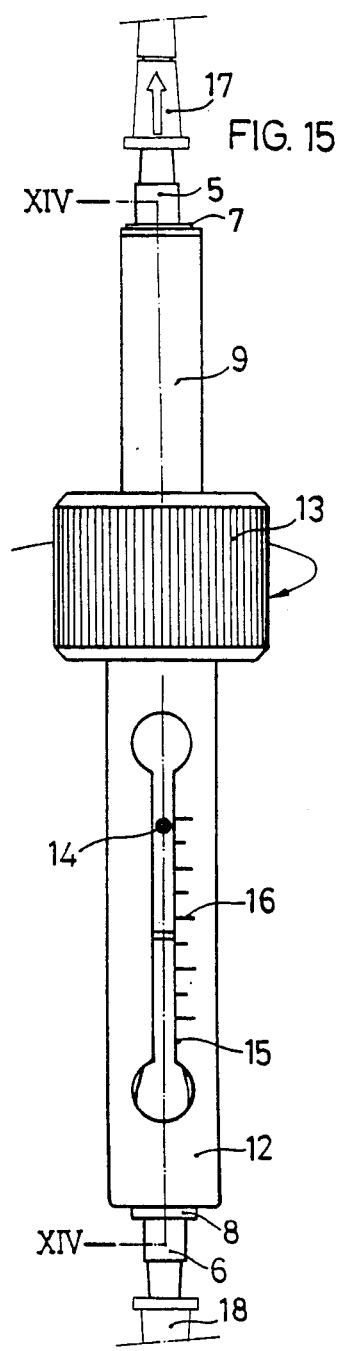

As shown in the figures, the present Patent of Invention is based on the arrangement of a flexible tubular member 1, in the interior of which there is disposed a cylindrical body 2 having a smaller diameter and the length of which is not critical, the operation of the valve being based on the principle that the annular clearance 3 between the outer tubular member 1 and the internal cylindrical member 2 may be varied by pulling the tubular member 1 by way of an axial force represented by the arrow 4 in FIG. 2. In this way, it is possible to vary said clearance, thereby varying the section of passage of the liquid being conducted by the tubular member 1, with it being possible to reach a complete closure, as shown in FIGS. 2 and 4, wherein there may be observed the position of said members in which the clearance 3 as been completely eliminated.

The method of producing the longitudinal pull on the tubular member 1 may be variable, a preferred embodiment according to the present Patent of Invention being the arrangement of extreme end pieces 5 and 6 having respective peripheral flanges 7 and 8. Said end pieces are firmly attached to the tubular member 1, in the ends of which they are inserted.

The unit formed by the tubular member 1 and end mouth pieces 5 and 6 is positioned in a tubular body 9 having an external thread and having a longitudinal flattened portion 10 and diametrally opposite thereto, a longitudinal groove 11.

An outer member 12 having a square or rectangular section and open on one side thereof receives in the interior thereof the tubular member 9, which may not rotate in the interior of said body 12 because of the engagement of the flat side 10 and the edges of the groove 11 with two opposite sides of said square sectioned body 12.

An adjusting nut 13 is mounted on the top end of the threaded tubular body 9, forming an abutment against the upper end of the square sectioned body 12. At the bottom end thereof, the square sectioned outer body 12 abuts the lower flange 8 of the end piece 6. With this arrangement, when the nut 13 is rotated, since this is axially fixed by abutting the edge of the square sectioned member 12, it causes axial movement of the threaded cylindrical body 9, which projects towards the outside, as shown in FIG. 14, the upper surface of the nut 13 abutting against the flange 7 of the upper end piece 5. Under these conditions, the flexible tubular member 1 is gradually stretched, thereby varying the radial clearance between said tubular member and the internal stoppering body 2, thereby providing the adjustable operation to which the valve is directed.

The threaded cylindrical body 9 may be provided on the outer surface thereof with an indicating mark or protuberance 14, moving along a slot 15 in the square sectioned body 12, there being provided graduation marks 16 on one of the edges of said slot 15, allowing a visual reference of the degree of opening of the valve to be had.

The valve is attached at the ends thereof to the supply tubes 17 and 18 of the medical apparatus to which it is applied.

In accordance with the present invention, it is also contemplated that the threaded mechanism for adjusting the liquid passage may be achieved by a two stage system, one being a coarse adjustment stage and the other a fine adjustment stage, such that the former allows a first coarse adjustment to be made towards the desired position, and the latter allows a final, accurate adjustment to be made.

As is obvious, there are many constructional details of the valve of the present Patent of Invention which may be variably embodied, without exceeding the scope of the present invention. Thus, for example, the methods of attaching the flexible tubular member to the end pieces and of the latter to the medical apparatus of interest, as well as the systems for producing the axial stretching of the tubular member, system of visual indication of the degree of opening, etc., which may be embodied by variations of the present invention, while remaining within the scope thereof.

Everything that does not affect, alter, change or modify the essence of the valve described hereinbefore will be variable for the effects of the present Patent.

I claim:

1. An adjustable valve for liquids comprising:
   a flexible tubular body having a first end and a second end, said body capable of elongation along the longitudinal axis;
   a substantially cylindrical rigid body, said rigid body having a diameter smaller than the inside diameter of said flexible tubular body, said rigid body provided within said flexible tubular body to form a radial clearance between said rigid body and the inside surface of said flexible tubular body; and
   means for elongating said flexible tubular body along the longitudinal axis about said rigid body, whereby elongation of said flexible tubular body reduces said radial clearance.

2. The adjustable valve of claim 1 further comprising a hollow end member at each end of said tubular body, said end member secured to each end of said tubular body and in fluid communication with said tubular body, and said end member including a radial flange for receiving the force of elongation from said elongating means.

3. The adjustable valve of claim 2 wherein said elongating means includes a rigid tubular body formed from a first threaded portion and a second threaded portion threaded to said first portion, said rigid tubular body positioned about said flexible tubular body and between said radial flanges of said end members.

4. The adjustable valve of claim 3 wherein said rigid tubular body includes a longitudinal slot.

5. The adjustable valve of claim 3 further comprising a rectangular sectioned outer member having a first end and a second end, said member internally receiving a segment of said rigid tubular body, said first end of said member abutting a radial flange and said second end of said member abutting said second portion of said rigid tubular body.

6. The adjustable valve of claim 5 wherein said segment of said rigid tubular body internally received by said outer member is configured to resist axial rotation with respect to said outer member.

7. The adjustable valve of claim 6 wherein said segment of said rigid tubular body internally received by said outer member includes a longitudinal slot.

8. The adjustable valve of claim 7 wherein said configured segment includes a substantially flattened area diametrically opposite said longitudinal slot.

9. The adjustable valve of claim 7 wherein said rectangular sectioned outer member includes an external longitudinal slot and said rigid tubular body internally received by said outer member includes an indicator protuberance viewable from said external longitudinal slot.

10. The adjustable valve of claim 9 wherein said outer member includes graduation indicia adjacent said external longitudinal slot.

* * * * *